(12) United States Patent
Newman

(10) Patent No.: US 9,381,065 B2
(45) Date of Patent: *Jul. 5, 2016

(54) TREATMENT OF HEADACHE

(71) Applicant: Serene Medical, Inc., San Ramon, CA (US)

(72) Inventor: James P. Newman, Redwood City, CA (US)

(73) Assignee: Serene Medical, Inc., San Ramon, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/599,161

(22) Filed: Jan. 16, 2015

(65) Prior Publication Data

US 2015/0141903 A1    May 21, 2015

Related U.S. Application Data

(63) Continuation of application No. 14/156,033, filed on Jan. 15, 2014, now Pat. No. 8,938,302, which is a continuation of application No. 12/605,295, filed on Oct. 23, 2009, now Pat. No. 8,666,498.

(60) Provisional application No. 61/108,820, filed on Oct. 27, 2008.

(51) Int. Cl.
| | |
|---|---|
| *A61N 1/00* | (2006.01) |
| *A61B 18/14* | (2006.01) |
| *A61N 5/06* | (2006.01) |
| *A61B 18/24* | (2006.01) |
| *A61M 5/00* | (2006.01) |
| *A61N 1/36* | (2006.01) |
| *A61B 18/00* | (2006.01) |

(52) U.S. Cl.
CPC ............. *A61B 18/1492* (2013.01); *A61B 18/24* (2013.01); *A61M 5/00* (2013.01); *A61N 1/36021* (2013.01); *A61N 1/36075* (2013.01); *A61N 5/0622* (2013.01); *A61B 2018/00321* (2013.01); *A61B 2018/00434* (2013.01); *A61B 2018/00577* (2013.01); *A61B 2018/00642* (2013.01); *A61B 2018/00702* (2013.01); *A61B 2018/00839* (2013.01); *A61N 1/36017* (2013.01)

(58) Field of Classification Search
CPC ............... A61B 18/1492; A61B 18/24; A61N 1/36021; A61N 1/36075; A61N 5/0622
See application file for complete search history.

(56) References Cited

U.S. PATENT DOCUMENTS

| | | | |
|---|---|---|---|
| 5,540,734 A * | 7/1996 | Zabara | ............................ 607/46 |
| 6,432,986 B2 * | 8/2002 | Levin | ............................ 514/330 |
| 6,706,016 B2 | 3/2004 | Cory et al. | |
| 6,735,475 B1 * | 5/2004 | Whitehurst et al. | ............ 607/46 |
| 2006/0153876 A1 * | 7/2006 | Sanders | ..................... 424/239.1 |
| 2009/0062886 A1 | 3/2009 | O'Handley et al. | |
| 2010/0114191 A1 | 5/2010 | Newman | |
| 2012/0071811 A1 * | 3/2012 | Ansarinia | ....................... 604/20 |

* cited by examiner

*Primary Examiner* — Robert N Wieland
(74) *Attorney, Agent, or Firm* — Levine Bagade Han LLP

(57) ABSTRACT

Headache treatment methods are described and include providing an energy delivery device; locating a secondary or higher-order branch of a postganglionic nerve that provides innervation for a patient's head, by identifying a target region of the patient's head that includes the nerve branch; positioning, within the target region, a portion of the energy delivery device; and applying, from the positioned portion of the energy delivery device to the target region, an amount of energy effective to result in a stimulation activity of the nerve branch; and, after observing the stimulated nerve branch activity, delivering, from the energy delivery device to the nerve branch, energy in an amount effective to reduce a headache severity in the patient.

20 Claims, 3 Drawing Sheets

TREATMENT OF HEADACHE

CROSS-REFERENCE TO RELATED APPLICATIONS

This application is a continuation of U.S. patent application Ser. No. 14/156,033 filed Jan. 15, 2014 (now U.S. Pat. No. 8,938,302), which is a continuation of U.S. patent application Ser. No. 12/605,295 filed Oct. 23, 2009 (now U.S. Pat. No. 8,666,498 issued Mar. 4, 2014), which claims the benefit of U.S. Provisional Application No. 61/108,820, filed on Oct. 27, 2008, the content of which is incorporated herein by reference in its entirety.

BACKGROUND OF THE INVENTION

1. Field

Embodiments disclosed herein relate to treatment of headache.

2. Description of the Related Art

Headache pain is highly prevalent amongst people worldwide. The World Health Organization estimates that one person in 20 has a headache everyday or almost every day. In addition, approximately 70% of adults in developed countries are afflicted with tension or "stress" headaches. The World Health Organization estimates that 240 million people worldwide each year are afflicted with migraine headaches. Headache pain can impose disabling hardships on afflicted individuals such as personal suffering, impaired quality of life, and impaired financial status. Headache pain, in some instances together with the constant fear of such pain, can damage an afflicted individual's family life, social life, workplace productivity, etc. Moreover, individuals who suffer long-term chronic headache pain can be predisposed to suffer other illnesses; for example, depression is three times more common in people afflicted with recurring migraine or severe headaches than in people who do not suffer from recurring migraine or severe headaches.

BRIEF SUMMARY OF THE INVENTION

In certain embodiments, a headache treatment method is provided. The method includes providing an energy delivery device; locating a secondary or higher-order branch of a postganglionic nerve that provides innervation for a patient's head, wherein the locating comprises: identifying a target region, of the patient's head, comprising the nerve branch; positioning, within the target region, a portion of the energy delivery device; and applying, from the positioned portion of the energy delivery device to the target region, an amount of energy effective to result in a stimulation activity of the nerve branch; and after observing the stimulated nerve branch activity, delivering, from the energy delivery device to the nerve branch, energy in an amount effective to reduce a headache severity in the patient.

In certain embodiments of the method, the headache severity comprises at least one of a degree of pain, a frequency, and a duration of the headache. In certain embodiments of the method, the nerve branch comprises a motor neuron. In certain embodiments of the method, the nerve comprises a sympathetic neuron. Certain embodiments of the method involve detecting the stimulated nerve branch activity with electromyography. Certain embodiments of the method involve detecting the stimulated nerve branch activity as nerve conduction between two electrodes. In certain embodiments of the method, the nerve branch comprises a tertiary or higher-order branch. Certain embodiments of the method also involve locating a sensory nerve provides innervation for the patient's head; and applying, from the positioned portion of the energy delivery device to the sensory nerve, an amount of energy effective to reduce the headache severity in the patient.

In certain embodiments of the method, the delivered energy comprises electromagnetic energy. In certain embodiments of the method, the delivered energy comprises at least one of ultrasound energy, heat energy, and cryogenic energy. In certain embodiments of the method, the delivered energy comprises at least one of an ultraviolet light energy, a blue light energy, an infrared light energy, an x-ray energy, a gamma-ray energy, and a microwave energy. In certain embodiments of the method, the amount of delivered energy effective to reduce the headache pain is effective to ablate the neuron.

In certain embodiments of the method, the motor neuron innervates a muscle selected from the group consisting of a frontalis muscle, a corrugator superculii muscle, an orbicularis oculi muscle, a procerus muscle, a nasalis muscle, a levator labii superioris muscle, a zygomaticus major muscle, a zygomaticus minor muscle, a levator anguii oris muscle, a modialus muscle, a platysma paris muscle, a platysma labialis muscle, a depressor labii inferioris muscle, a depressor anguli oris muscle, a platysma pars modialaris muscle, a platysma pars labialis muscle, a platysma pars mandibularis muscle, a temporalis muscle, an occipatalis muscle, a risorius muscle, a masseter muscle, a splenius capitus muscle, a stylohyoid muscle, a suboccipital muscle, a digastric muscle, a buccinator muscle, a sternocleidomastoid muscle, a levator scapulae muscle, a scalenus medius muscle, a scalenus anterior muscle, a trapezius muscle, and an omohyoid muscle.

In certain embodiments of the method, the nerve is selected from at least one of a facial nerve, an abducens nerve, an oculomotor nerve, a trochlear nerve, a trigeminal nerve, a glossopharangeal nerve, a hypoglossal nerve, and an accessory nerve. In certain embodiments of the method, the nerve branch is a branch of a facial nerve selected from a temporal branch, a zygomatic branch, a buccal branch, a mandibular branch, and a cervical branch. In certain embodiments of the method, the nerve branch is selected from at least one of a superior division of the oculomotor nerve and an inferior division of the oculomotor nerve. In certain embodiments of the method, the nerve branch is a mandibular branch of the trigeminal nerve. In certain embodiments of the method, the nerve branch is a mylohyoid branch of the mandibular branch. In certain embodiments of the method, the nerve branch is a pharyngeal branch of the glossopharyngeal nerve. In certain embodiments of the method, the nerve branch is a branch of the hypoglossal nerve selected from a meningeal branch, a thyrohyoid branch, a descending branch, and a muscular branch in certain embodiments of the method, the nerve branch is an angular nerve. In certain embodiments of the method, the sensory nerve comprises at least one of a second occipital nerve, a third occipital nerve, a zygomaticotemporal nerve, a trigeminal nerve, a glossopharyngeal nerve.

In certain embodiments, another method, of treating headache, is provided. The other method includes providing an energy delivery device; locating a secondary or higher-order branch of a postganglionic nerve that provides innervation for a patient's head, wherein the locating comprises: identifying a target region, of the patient's head, comprising the nerve branch; positioning, within the target region, a portion of the energy delivery device; and applying, from the positioned portion of the energy delivery device to the target region, an amount of energy effective to result in a stimulation activity of the nerve branch; after observing the stimulated nerve branch activity: delivering, from the energy delivery device to the nerve branch, energy in an amount effective to reduce a headache severity in the patient; and administering, to a target area of the patient's head comprising a motor neuron, a neurotoxin; wherein, in combination, the amount of delivered energy and the amount of administered neurotoxin are effective to reduce a headache severity in the patient.

In certain embodiments of the other method, the headache severity comprises at least one of a degree of pain, a frequency, and a duration of the headache. In certain embodiments of the other method, the nerve branch comprises a motor neuron, a sympathetic neuron, or a tertiary or higher-order branch. In certain embodiments of the other method, the method further includes at least one of detecting the stimulated nerve branch activity with electromyography, and detecting the stimulated nerve branch activity as nerve conduction between two electrodes.

In certain embodiments of the other method, the method further includes locating a sensory nerve innervating the patient's head, and applying, from the positioned portion of the energy delivery device to the sensory nerve, an amount of energy effective to reduce the headache severity in the patient. In certain embodiments of the other method, the sensory nerve comprises at least one of a second occipital nerve, a third occipital nerve, a zygomaticotemporal nerve, a trigeminal nerve, a glossopharyngeal nerve.

In certain embodiments of the other method, the delivered energy comprises at least one of ultrasound energy, heat energy, cryogenic energy, electromagnetic energy, ultraviolet light energy, a blue light energy, an infrared light energy, an x-ray energy, a gamma-ray energy, and a microwave energy. In certain embodiments of the other method, the amount of delivered energy effective to reduce the headache pain is effective to ablate the neuron.

In certain embodiments of the other method, the motor neuron innervates a muscle selected from the group consisting of a frontalis muscle, a corrugator superculii muscle, an orbicularis oculi muscle, a procerus muscle, a nasalis muscle, a levator labii superioris muscle, a zygomaticus major muscle, a zygomaticus minor muscle, a levator anguii oris muscle, a modialus muscle, a platysma paris muscle, a platysma labialis muscle, a depressor labii inferioris muscle, a depressor anguli oris muscle, a platysma pars modialaris muscle, a platysma pars labialis muscle, a platysma pars mandibularis muscle, a temporalis muscle, an occipatalis muscle, a risorius muscle, a masseter muscle, a splenius capitus muscle, a stylohyoid muscle, a suboccipital muscle, a digastric muscle, a buccinator muscle, a sternocleidomastoid muscle, a levator scapulae muscle, a scalenus medius muscle, a scalenus anterior muscle, a trapezius muscle, and an omohyoid muscle.

In certain embodiments of the other method, the nerve is selected from at least one of a facial nerve, an abducens nerve, an oculomotor nerve, a trochlear nerve, a trigeminal nerve, a glossopharangeal nerve, a hypoglossal nerve, and an accessory nerve. In certain embodiments of the other method, the nerve branch comprises a branch of a facial nerve selected from a temporal branch, a zygomatic branch, a buccal branch, a mandibular branch, and a cervical branch. In certain embodiments of the other method, the nerve branch is selected from at least one of a superior division of the oculomotor nerve and an inferior division of the oculomotor nerve.

In certain embodiments of the other method, the nerve branch comprises a mandibular branch of the trigeminal nerve, a mylohyoid branch of the mandibular branch, or a pharyngeal branch of the glossopharyngeal nerve. In certain embodiments of the other method, the nerve branch comprises a branch of the hypoglossal nerve selected from a meningeal branch, a thyrohyoid branch, a descending branch, and a muscular branch. In certain embodiments of the other method, the nerve branch comprises an angular nerve.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION OF THE INVENTION

Figure 1:
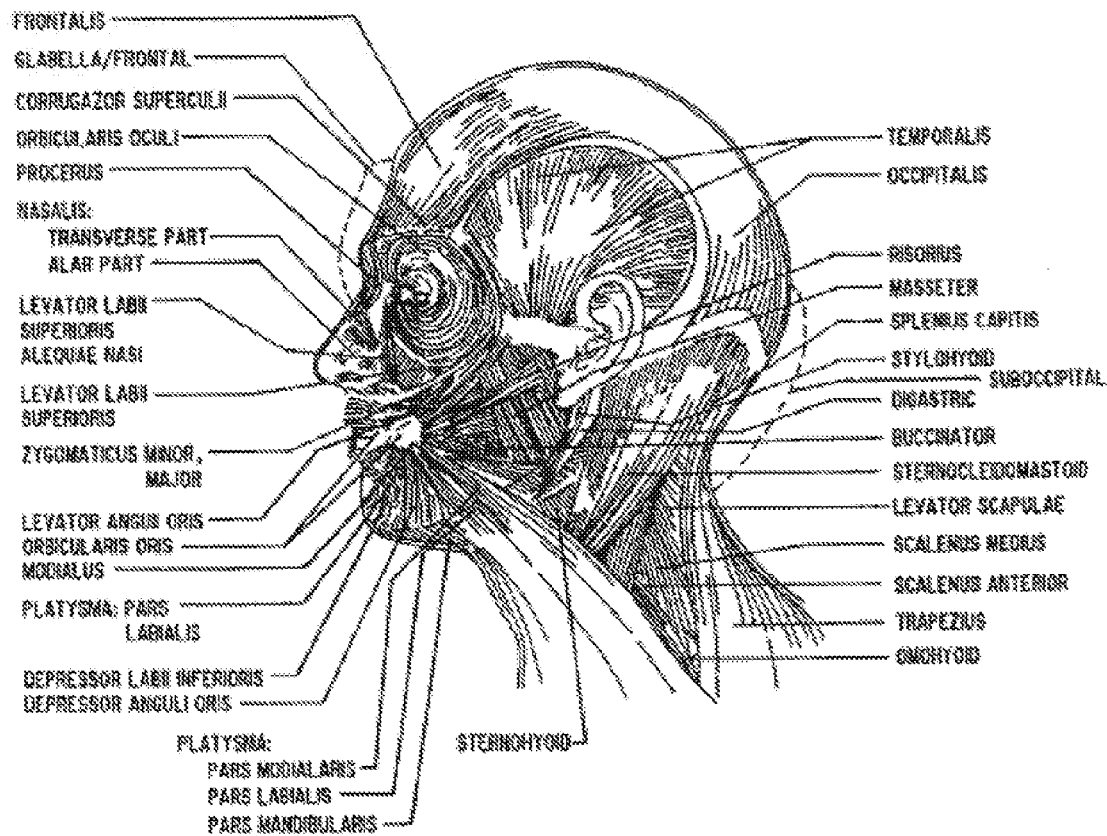
FIG. 1 is a stylized illustration of certain muscles of a human head.

The international headache society has classified headache disorders and facial pain into many groups. The groups include: migraine headache; tension headache; cluster headache; miscellaneous headache unassociated with structural lesions; headache associated with head trauma; and headache associated with vascular disorders. The groups also include headache associated with non-vascular intracranial disorder; headache associated with substances or their withdrawal; headache associated with non-cephalic infections; headache associated with metabolic disorders; headache associated with disorders of facial or cranial structures; headache associated with cranial neuralgias; and non-classifiable headache.

Vascular headaches include a variety of conditions resulting from head pain generating events at interfaces between blood vessels and nerve fibers. For instance, afferent nociceptive nerve fibers enervating meningeal blood vessels can become activated in response to inflammatory and related events, resulting in pain. A common vascular headache is migraine headache, which can last 72 hours or more. Migraine headache characteristics include unilateral or bilateral head pain of moderate to severe intensity which can be associated with nausea, vomiting, sensitivity to light, sensitivity to sound, and visual disturbances. The trigeminal-vascular system is believed to play a role in the genesis of many migraine headaches.

Vascular headaches also include "cluster" headache, which are commonly characterized by frequent, transient attacks of a high-intensity, unilateral head pain. Cluster headache pain is often described as a burning, stabbing, or piercing sensation localized behind the eye or in the region, and can manifest pain in the face, temple, nose, cheek, and/or upper gum on the affected side. Cluster headaches can be accompanied by autonomic symptoms (e.g., lacrimation and nasal congestion), can occur several times in a single day over the course of several weeks or months, and can return after disappearing for several weeks, months, or years. Although uncertain, the trigeminal-autonomic system appears to play a role in the genesis of cluster headache. Cluster headache is a neurological disease that involves, as its most prominent feature, an immense degree of pain. "cluster" refers to the tendency of these headaches to occur periodically, with active periods interrupted by spontaneous remissions.

Tension headaches (or "tension-type headaches") are frequently characterized by bilateral head pain of mild to moderate intensity, and tension headaches can be chronic. Tension headache pain is often described as a pressing, dull, aching, and/or pulsating pain. The genesis of many tension headaches appears to involve the myo-facial system, and tension headaches can be caused by, for example, the tightening of facial and neck muscles, teeth clinching, teeth grinding, and poor posture. Tension headaches are the most common type of primary headaches. The pain can radiate from the neck, back, eyes, or other muscle groups in the body.

Trigeminal neuralgia comprises an affliction of the trigeminal nerve, and results in severe head pain. Trigeminal neuralgia pain is often described as quick bursts of lightning-bolt, machine-gun, or electric-shock type of pain which usually affects one side of the head or face in short bursts lasting a few seconds and repeated many times over the course of an attack. Occipital neuralgia comprises an affliction of the occipital nerves, and results in severe head pain, which frequently originates in the neck and spreads up the forehead and scalp. Occipital neuralgia can be caused by physical stress, trauma to or compression of the greater or lesser occipital nerves, tumors involving the second and third cervical dorsal root, or repeated contractions of neck muscles.

Cervicogenic headaches are frequently characterized by pain signals from nerves originating in neck structures, such as the joints, ligaments, muscles, and cervical discs, which synapse in the same brainstem nuclei as nerve fibers of the trigeminal nerve. Since the trigeminal nerve is responsible for the perception of head pain, the patient experiences the symptoms of headache pain. Many cervicogenic headaches are characterized by pain similar to tension headache pain, but some cervicogenic headaches are characterized by pain similar to migraine or cluster headache pain.

Several approaches for treating head pain associated with a wide variety of headaches have been developed, and can involve preventative treatment, treatment to relieve specific symptoms, and/or abortive treatment. For instance, serotonin receptor agonists, given early at the onset of pain associated with migraine headache, can be effective in up to 70% of patients. But serotonin receptor agonists are frequently only partially effective at attenuating migraine headaches, and rebound pain frequently occurs as drug levels fall. Moreover, serotonin agonists frequently become ineffective over repeated usages, and side effects of serotonin receptor agonists include dizziness, shortness of breath, and chest pain. Other drugs used to prevent migraines include beta-blockers, calcium channel blockers, nsaids, antidepressants, anticonvulsants, and neurotoxins. Electric stimulation of certain head or face nerves, such as an occipital nerve, a great auricular nerve, a supra-clavicular nerve, and a cervical nerve, has been used to treat a variety of headache types, including migraines. Another approach to preventing headaches is educating patients to recognize and avoid headache triggers which can include weather changes, bright light, strong odors, and stress. Again, these methods are typically only partially effective, and at best reduce the frequency of headaches.

Abortive treatments for cluster headaches include, e.g., inhalation of 100% oxygen, occipital nerve block, 5ht1 antagonists, and ergotamines. Preventative therapy is an important approach for treating cluster headaches, and drugs used in such treatments include beta-blockers, tricyclic antidepressants, anticonvulsants, cyproheptadine, and nsaids. But these approaches are also of limited effectiveness.

Approaches for treating tension headache include, e.g., symptomatic and/or abortive treatment involving administration of drugs such as aspirin, acetaminophen, and nsaids. Occasionally, tricyclic and antidepressants are used to treat severe and/or chronic tension headache. Approaches for treating head pain associated with trigeminal neuralgia include analgesic agents, which have an approximate 50% success rate and analgesic drugs, such as opioids or nsaids.

Given the prevalence of headache pain and given that, today, there does not appear to be a class of drugs or a treatment regimen reliably effective for relieving headache pain, there is a need for novel and effective therapies preventing or alleviating headache pain.

Neuromuscular Anatomy of the Head

Figure 2:
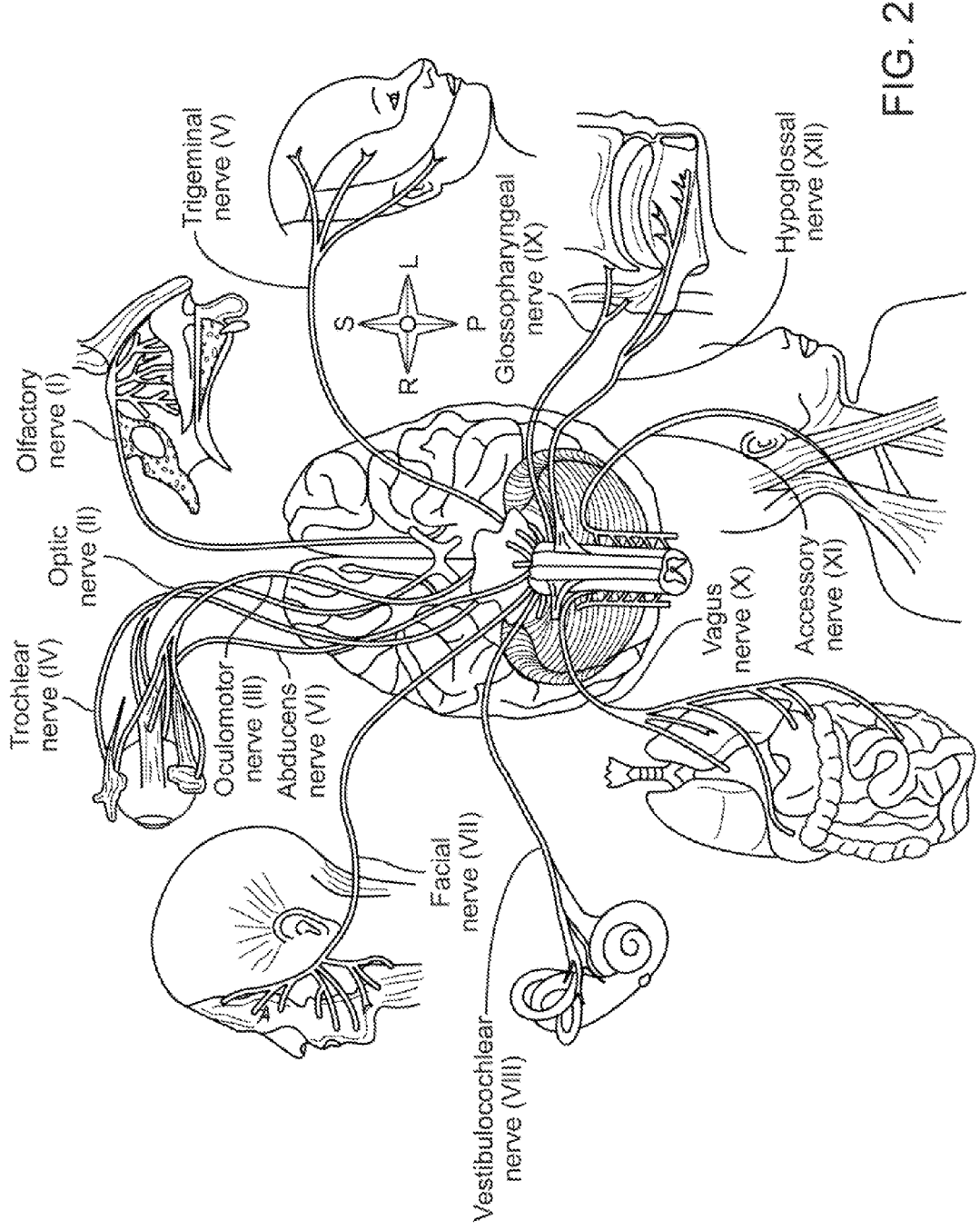
FIG. 2 is a stylized illustration of certain nerves of a human head.
Figure 3:
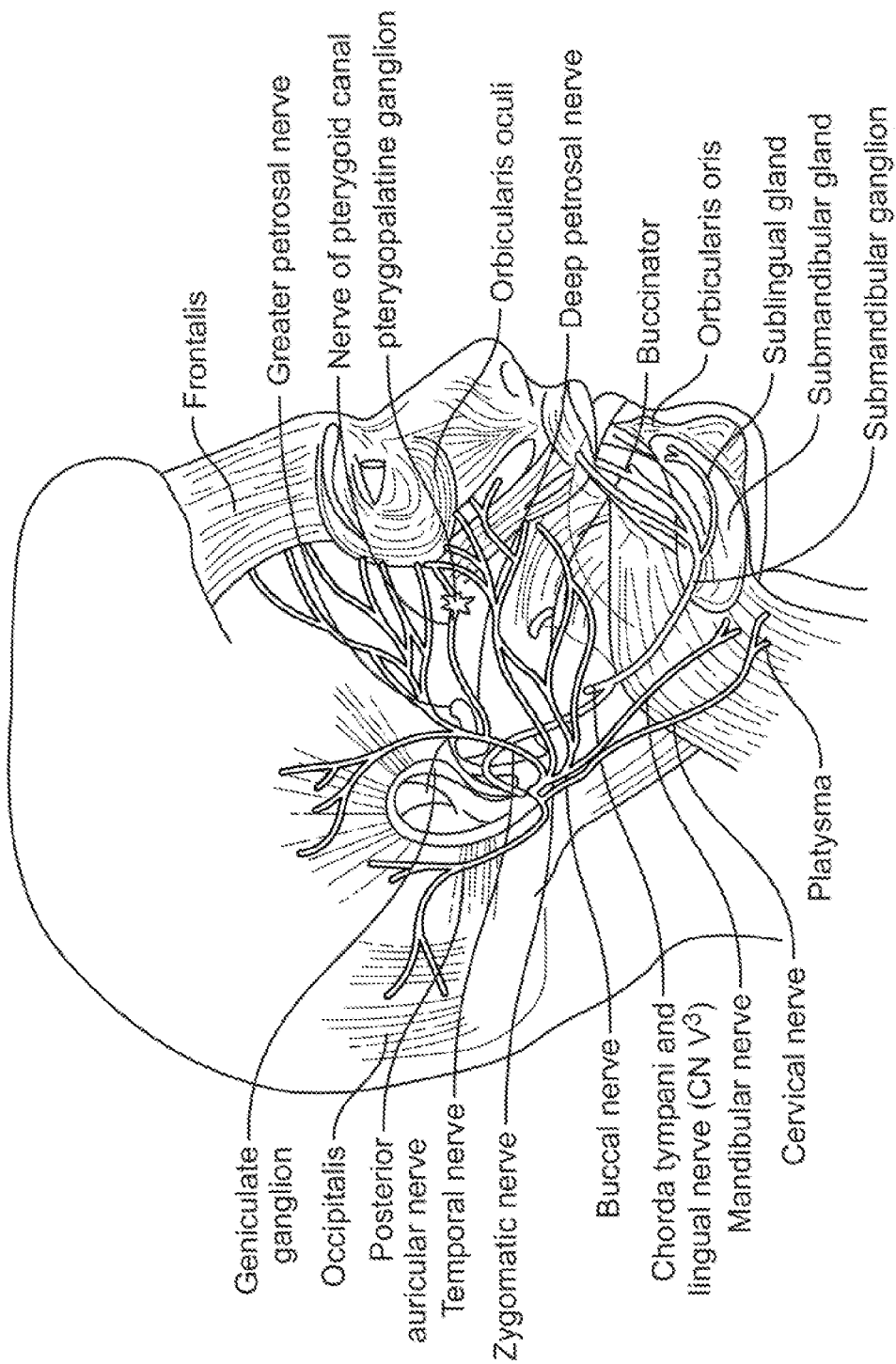
FIG. 3 is a stylized illustration of certain nerves of a human head.

FIGS. 1 and 3 illustrate certain muscles in a human head. FIGS. 2 and 3 illustrate the 12 pairs cranial nerves, which originate from the brain and innervate their respective target tissues and certain branch nerves thereof. The views shown in FIGS. 1-3 and the descriptions of FIGS. 1-3 herein are not intended to be strictly anatomically accurate or complete, but rather illustrative, in a non-limiting manner, of certain features of the present disclosure. For example, certain embodiments provide methods for reducing headache severity in a patient comprising administering pain reducing energy to a secondary or higher order postganglionic nerve branch that provides innervation for an area of the patient's head, the area comprising, but not limited to, nerves and muscles illustrated in FIGS. 1-3. Certain embodiments provide methods for reducing headache severity in a patient comprising administering pain reducing energy to a secondary or higher order postganglionic nerve branch that provides innervation for an area of the patient's head and administering a neurotoxin to an area of the patient's head, the area comprising, but not limited to, nerves and muscles illustrated in FIGS. 1-2. As used herein, "a secondary or higher-order branch of a neuron" refers to the following: if one follows a nerve from its cell body, along its axon to its dendrites, from proximal to distal, a first branch point of the axon is called a "primary branch point," a second branch point of the axon is called a "secondary branch point." a "higher-order" branch means a higher numbered branch point relative to some lower numbered branch point referred to in a context. For example, in the context of "secondary or higher order," higher order would refer to a tertiary or higher numbered thing, and in the context of "primary or higher order, higher order would refer to a secondary or higher numbered thing.

Referring to FIGS. 1-2, the olfactory nerve transmits certain odor information to the brain. The optic nerve transmits certain visual information to the brain. The oculomotor nerve innervates, e.g., the levator palpebrae superioris, superior rectus, medial rectus, inferior practice, and inferior oblique muscles, which collectively perform most eye movements. The trochlear nerve innervates, e.g., the superior oblique muscle, which is involved in depressing, pulling laterally, and intorting the eyeball.

The trigeminal nerve receives certain sensory information from the face and innervates certain facial and mastication muscles. The abducens nerve provides innervation for, e.g., the lateral rectus muscle, which is involved in abducting the eye. The facial nerve is involved in providing motor innervation for certain muscles of the face involved in facial expression. The facial nerve also receives certain taste information from the anterior ⅔ of the tongue and is involved in providing secretomotor innervation to certain salivary glands and the lacrimal gland.

The vestibulocochlear nerve is involved in balance, movement, and sensing sound, rotation, and gravity. The glossopharyngeal nerve receives certain taste information from the posterior ⅓ of the tongue, and is involved in providing secretomotor innervation to the parotid gland and motor innervation to the stylopharyngeus. The vagus nerve is involved in providing motor innervation to certain laryngeal and pharyngeal muscles, and the vagus nerve also provides certain parasympathetic fibers to thoracic and abdominal viscera, down to the splenic flecture. The vagus nerve further receives certain taste information from the epiglottis. The accessory nerve is involved in providing control of muscles of the neck and provides some overlapping functions of the vagus nerve. The hypoglossal nerve is involved in swallowing and speech articulation, and is involved in providing motor innervation for certain glossal muscles.

The frontalis muscle originates at the superior curved line of occipit and the mastoid portion of the temporal bone, and inserts at the eyebrow and root of nose. The frontalis muscle is involved in moving the scalp and raising the eyebrows. The temporal muscle originates at the temporal fossa and fascia and inserts at the coronoid process of the lower jaw. The temporal muscle is involved in raising the lower jaw. The masseter muscle originates at the upper portion of the superior maxillary bone and inserts at the lower portion of the inferior maxillary bone. The masseter muscle is involved in raising the lower jaw.

The risorius muscle originates at the fascia over the parotid gland and inserts at the angle of the mouth. The risorius muscle is involved in drawing back the corners of the mouth. The splenius capitus muscle originates at the lower half of the ligamentum nuchae, the spinous process of the seventh cervical vertebra, and at the spinous processes of the upper three or four thoracic vertebrae, and the splenius capitis inserts at the sternocleidomastoideus, at the mastoid process of the temporal bone, and at the surface on the occipital bone just below the lateral third of the superior nuchal line. The splenius capitis muscle is involved in head extension and head rotation.

The stylohyoid muscle originates at the styloid process and inserts at the hyoid bone. The stylohyoid muscle is involved in depressing the jaw and raising the hyoid bone. The suboccipital muscle refers to muscles located below the occipital bone, including the rectus capitis posterior major, rectus capitis posterior minor, obliquus capitis inferior, and obliquus capitis superior. The rectus capitis posterior major originates at the spinous process of the epistropheous and inserts below the superior ridge of the occipit. The rectus capitis posterior major is involved in rotating the atlas and cranium. The rectus capitis posterior minor originates at the posterior arch of the atlas and inserts below the inferior ridge of the occipit. The rectus capitis posterior minor is involved in drawing back the head. The obliquus capitis inferior originates at the spinous process of atlas and inserts at the transverse process of atlas. The obliquus capitis inferior is involved in rotating atlas on axis. The obliquus capitis superior originates at the transverse process of atlas and inserts between regions of occipit. The obliquus capitis superior is involved in drawing back the head. The digastric muscle originates at the mastoid and lower jaw and inserts at the hyoid bone. The digastric muscle is involved in depressing the jaw in raising the hyoid bone. The buccinator muscle arises at alveolar borders of the superior and inferior maxillary bone and inserts at the orbicularis oris at the angle of the mouth. The buccinator muscle is involved in keeping food between grinders and in whistling.

The sternocleidomastoid muscle passes obliquely across the neck. It originates at the medial third of the clavicle and inserts at the mastoid process. The sternocleidomastoid muscle is involved in bending the head forward and to one side. The levator scapulae muscle arises at tendinous slips from the transverse processes of the atlas and axis and from the posterior tubercles of the transverse processes of the third and fourth cervical vertebrae and it inserts at the vertebral border of the scapula, between the medial angle and the triangular smooth surface at the root of the spine. The levator scapulae muscle is involved in shrugging and in raising the medial angle of the scapula.

The scalenus medius muscle originates at the posterior tubercles of transverse processes of the lower six cervical vertebrae and insert at the upper surface of the first rib. The scalenus medius muscle is involved in the elevating the first rib and rotating the neck. The scalenus anterior muscle originates at the anterior tubercles of transverse processes of the third to six cervical vertebra and inserts at tubercle on inner border of the first rib. The scalenus anterior is involved in flexing the head sideways and forward.

The trapezius muscle arises at the external occipital protuberance and the medial third of the superior nuchal line of the occipital bone (both in the back of the head), at the ligamentum nuchae, at the spinous process of the seventh cervical (both in the back of the neck), and at the spinous processes of all the thoracic vertebrae, and at the corresponding portion of the supraspinal ligament (both in the upper back). The trapezius muscle inserts at the posterior border of the lateral third of the clavicle, at a tubercle at the apex of this smooth triangular surface, and at the medial margin of the acromion, and into the superior lip of the posterior border of the spine of the scapula. The trapezius muscle is involved in scapular elevation, retraction, and depression.

The omohyoid muscle originates at the upper border of the scapula and inserts at the hyoid bone. The omohyoid muscle is involved in depressing and retracting the hyoid bone. The corrugator supercilii originates at the medial end of the superciliary arch and inserts at deep surfaces of the skin, above the middle of the orbital arch. The corrugator is involved in drawing downward and medialward the eyebrow, producing the vertical wrinkles of the forehead. It is known as the "frowning" muscle.

The orbicularis oculi is a sphincter muscle of the eyelids. It originates at, e.g., the nasal part of the frontal bone, at the frontal process of the maxilla in front of the lacrimal groove, and at the medial palpebral ligament. The palpebral portion of the muscle inserts at the lateral palpebral raphe. The orbital portion comprises lower fibers that form an ellipse at the lateral palpebral commissure, and the upper fibers of this portion blend with the frontalis and corrugator muscles. The lacrimal part (tensor tarsi) inserts at the superior and inferior tarsi medial to the puncta lacrimalia. The orbicularis oculi is involved in closing the eye. When the entire muscle is brought into action, the skin of the forehead, temple, and cheek is drawn toward the medial angle of the orbit, and the eyelids are firmly closed. The skin then forms folds, especially radiating from the lateral angle of the eyelids; these folds become permanent in old age, and form the so-called "crow's feet."

The procerus muscle originates as tendinous fibers at the fascia covering the lower part of the nasal bone and upper part of the lateral nasal cartilage and inserts at the skin over the lower part of the forehead between the two eyebrows, its fibers decussating with those of the frontalis. The procerus muscle is involved in pulling apart skin between the eyebrows, which assists in flaring the nostrils.

The nasalis muscle includes transverse and alar parts. The transverse part originates at the maxilla, above and lateral to the incisive fossa, and its fibers proceed upward and medially, expanding into a thin aponeurosis which is continuous on the bridge of the nose with that of the muscle of the opposite side, and with the aponeurosis of the procerus. The alar part is attached at one end to the greater alar cartilage, and at the other to the integument at the point of the nose.

The levator labii superioris (or quadratus labii superioris) originates at the side of the nose and inserts at the greater alar cartilage and skin of the nose and at the lateral part of the upper lip, blending with the infraorbital head and with the orbicularis oris. The zygomatic muscle arises at the malar bone and inserts at the orbicularis oris at the angle of the mouth. The zygomaticus muscle is involved in drawing upwards and backwards the corners of the mouth. The levator anguli oris muscle originates at the canine fossa, immediately below the infraorbital foramen and inserts at the angle of the mouth, intermingling with the zygomaticus, triangularis, and orbicularis oris.

The orbicularis oris comprises numerous strata of muscle fibers surrounding the orifice of the mouth, the muscle fibers are derived partly from other facial muscles which insert into the lips and partly from fibers proper to the lips. In addition, certain fibers connect the orbicularis oris muscle with the maxilae and the septum of the nose and with the mandible.

The platysma is a superficial muscle that overlaps the sternocleidomastoid. It originates at the fascia covering the upper parts of the pectoralis major and deltoideus; and inserts at the bone below the oblique line, at the skin and subcutaneous tissue of the lower part of the face, many of these fibers blending with the muscles about the angle and lower part of the mouth. Sometimes platysma muscle fibers can be traced to the zygomaticus or to the margin of the orbicularis oculi.

The depressor labii inferioris (or quadratus labii inferioris) is a facial muscle involved in lowering the bottom lip. It originates at the oblique line of the mandible and inserts at the skin of the lower lip, blending in with the orbicularis oris muscle. At its origin, the depressor labii is continuous with the fibers of the platysma muscle. The depressor labii inferioris is involved in depressing the lower lip. The depressor anguli oris originates at the oblique line of the mandible and inserts, by a narrow fasciculus, at the angle of the mouth. The depressor anguli oris is involved in frowning.

The sternohyoid muscle is a thin, narrow muscle attaching the hyoid bone to the sternum, one of the paired strap muscles of the infrahyoid muscles, and it is involved in depressing the hyoid bone. The sternohyoid muscle originates at the posterior border of the medial end of the clavicle, at the posterior sternoclavicular ligament, and at the upper and posterior part of the manubrium sterni and inserts, by short tendinous fibers, at the lower border of the body of the hyoid bone.

The lesser occipital nerve or small occipital nerve is a spinal nerve arising between the first and second cervical vertebrae, along with the greater occipital nerve. It innervates the scalp in the lateral area of the head behind the ear, and arises from the lateral branch of the ventral ramus of the second cervical nerve, sometimes also from the third; it curves around and ascends along the posterior border of the sternocleidomastoideus. Near the cranium it perforates the deep fascia. It continues upward along the side of the head behind the auricula, supplying the skin and communicating with the greater occipital, the great auricular, and the posterior auricular branch of the facial nerve. The smaller occipital varies in size, and is sometimes duplicated. It gives off an auricular branch, which supplies the skin of the upper and back part of the auricula, communicating with the mastoid branch of the great auricular. This branch is occasionally derived from the greater occipital nerve.

The greater occipital nerve is a spinal nerve arising from the dorsal primary rami of cervical spinal nerve two, between the first and second cervical vertebrae, along with the lesser occipital nerve. It is involved in innervating the scalp at the top of the head, over the ear, and over the parotid glands. The zygomatic-temporal nerve arises in the pterygopalatine fossa. It enters the orbit by the inferior orbital fissure, and divides into two branches, the zygomaticotemporal nerve and zygomaticofacial nerve. The zygomatic nerve carries sensory fibers from the skin. It also carries post-synaptic parasympathetic fibers (originating in the pterygopalatine ganglion) to the lacrimal nerve via a communication. These parasympathetic fibers come from the facial cranial nerve, and are involved in providing innervation for the lacrimal gland.

The trigeminal nerve is involved in providing sensation in the face. Sensory information from the face and body is processed by parallel pathways in the central nervous system. The fifth nerve is primarily a sensory nerve, but it also has certain motor functions. The trigeminal nerve is the largest of the cranial nerves, and its name derives from the fact that it has three major branches: the ophthalmic nerve ($V.sub.1$), the maxillary nerve ($V.sub.2$), and the mandibular nerve ($V.sub.3$). The mandibular nerve has both sensory and motor functions. The three branches converge on the trigeminal ganglion (also called the semilunar ganglion or gasserian ganglion), which contains the cell bodies of incoming sensory nerve fibers. The trigeminal ganglion is, in certain aspects, analogous to the dorsal root ganglia of the spinal cord, which contain the cell bodies of incoming sensory fibers from the rest of the body. From the trigeminal ganglion, a large sensory root enters the brainstem at the level of the pons. Immediately adjacent to the sensory root, a smaller motor root emerges from the pons at the same level. Motor fibers pass through the trigeminal ganglion on their way to peripheral muscles, their cell bodies located in the motor nucleus of the fifth nerve, deep within the pons. Motor fibers are also distributed (together with sensory fibers) in branches of the mandibular nerve.

The areas of cutaneous distribution (dermatomes) of the three branches of the trigeminal nerve generally have sharp borders with relatively little overlap (unlike dermatomes in the rest of the body, which show considerable overlap). Injection of local anesthetics such as lidocaine results in the loss of sensation from well-defined areas of the face and mouth. For example, the teeth on one side of the jaw can be numbed by injecting the mandibular nerve.

The ophthalmic, maxillary and mandibular branches leave the skull through three separate foramina: the superior orbital fissure, the foramen rotundum and the foramen ovale. The ophthalmic nerve carries certain sensory information from the scalp and forehead, the upper eyelid, the conjunctiva and cornea of the eye, the nose (including the tip of the nose), the nasal mucosa, the frontal sinuses, and parts of the meninges (the dura and blood vessels). The maxillary nerve carries certain sensory information from, e.g., the lower eyelid, cheek, nose, upper lip, upper teeth, upper gums, nasal mucosa, palate of the pharynx, roof of the pharynx, sphenoid sinus, and parts of the meninges. The mandibular nerve carries certain sensory information from, e.g., the lower lip, the lower teeth, the lower gums, the chin, the jaw (except the angle of the jaw), parts of the external ear, and parts of the meninges. The mandibular nerve carries certain touch/position and certain pain/temperature sensation from the mouth, and some of its branches, e.g., the lingual nerve, carries multiple types of nerve fibers that do not originate in the mandibular nerve.

The glossopharyngeal nerve is the ninth pair of twelve pairs of cranial nerves. It exits the brainstem out from the sides of the upper medulla, just rostral (closer to the nose) to the vagus nerve. The glossopharyngeal nerve receives certain sensory fibers from the posterior ⅓ of the tongue, the tonsils, the pharynx, the middle ear, and the carotid sinus. It supplies some parasympathetic fibers to the parotid gland via the otic ganglion, and it supplies some motor fibers to stylopharyngeus muscle. It also contributes to the pharyngeal plexus.

From the medulla oblongata, the glossopharyngeal nerve passes laterally across the flocculus, and leaves the skull through the central part of the jugular foramen, in a separate sheath of the dura mater, lateral to and in front of the vagus and accessory nerves. Within the jugular foramen, the glossopharyngeal nerve forms the superior ganglion, and the glossopharyngeal nerve is also associated with an inferior ganglion.

In its passage through the jugular foramen, it grooves the lower border of the petrous part of the temporal bone; and, at its exit from the skull, passes forward between the internal jugular vein and internal carotid artery. It descends in front of the latter vessel, and beneath the styloid process and the muscles connected with it, to the lower border of the stylopharyngeus. It then curves forward, forming an arch on the side of the neck and lying upon the stylopharyngeus and middle pharyngeal constrictor muscle. From there it passes under cover of the hypoglossal muscle, and is distributes to the palatine tonsil, the mucous membrane of the fauces and base of the tongue, and the mucous glands of the mouth.

Branches of the glossopharyngeal nerve include tympanic, stylopharyngeal, sonsillar, nerve to carotid sinus, branches to the posterior third of tongue, lingual branches, and vagus nerve branches.

Energy Generating Units

In certain embodiments, an energy delivery device can comprise at least one energy generating unit configured to provide electrical energy. In certain embodiments, an energy delivery device can comprise a backup energy generating unit configured to provide electrical energy in case a primary energy delivery device fails. In certain embodiments, an energy generating unit can be configured to provide electromagnetic energy of a variety of wavelengths, including gamma rays, x-rays, ultraviolet, blue, red, visible, infrared, radio, microwave wavelengths, and combinations thereof. In certain embodiments, an energy generating unit can be configured to provide ultrasonic energy. In certain embodiments, an electrical generating unit can be configured to provide electrical energy. In certain embodiments, an electrical generating unit can be configured to provide heat energy. In certain embodiments, an electrical generating unit can be configured to provide cryogenic energy. In certain embodiments, an electrical generating unit can be configured to provide other types of energy known to those of skill in the art.

In certain embodiments, energy generating units provide laser energy. Exemplary laser generating units include argon lasers, KTP lasers, Nd:YAG lasers, excimer lasers, alexandrite lasers, holmium:YAG lasers, Er:YAG, Er:YSGG, infrared gas lasers, ArF excimer lasers, XeCl excimer lasers, nitrogen lasers, and Nd:YLF lasers.

Electrode Probes

In certain embodiments, the energy delivery device can comprise an electrode probe, coupled to an energy generating unit, the electrode probe carrying one or multiple electrodes configured to deliver energy provided by the energy generating unit in amounts and temporal patterns effective to stimulate an activity of a motor nerve, a sensory nerve, a muscle, or a combination thereof or effective to inhibit, permanently or temporarily, an activity of a motor nerve, a sensor nerve, a muscle, or a combination thereof. In certain embodiments, an energy delivery device can comprise an electrode probe coupled to an energy generating unit, the electrode probe carrying one or multiple electrodes configured to deliver energy provided by the energy generating unit in amounts and temporal patterns effective to ablate a motor nerve and/or a sensory nerve.

In certain embodiments, an electrode probe can comprise one or more of a variety of cross-sectional shapes and forms, such as circular, rectangular, elliptical cross, conical, pyramidal, solid, and hollow. Surfaces of an electrode probe can comprise one or more of a variety of shapes and forms, such as smooth, textured, flat, concave, and convex. A longitudinal shape of an electrode probe can comprise one or more of a variety of forms, such as straight, arced, bent, or a combination thereof. In certain embodiments, an electrode probe can comprise a needle shape that allows for efficient percutaneous penetration into muscle and other tissues.

In certain embodiments, an electrode probe can comprise a penetration-depth measuring and/or limiting device, such as an adjustable or non-adjustable collar positioned at a desired distance from an end portion of an electrode probe configured for percutaneous insertion into muscle of a patient.

In certain embodiments, an electrode probe comprises a single tip for single-point, percutaneous penetration of muscle and other tissue. In certain embodiments, an electrode probe comprises a single tip configured for positioning at a skin surface. In certain embodiments, an electrode probe comprises multiple tips; some or all of which can be configured for percutaneous penetration and some or all of which can be configured for superficial positioning at a skin surface.

In certain embodiments, an electrode probe, an auxiliary probe, or both, of an energy delivery device, can comprise one or a plurality of sensors. Exemplary sensors include temperature sensors, energy conduction sensors, energy impedance sensors, voltage sensors, wattage sensors, amperage sensors, and optical sensors. In certain embodiments, information gathered by such sensors is indicative of an identity of tissues (e.g., adipose, bone, nerve, and muscle tissue) in a proximity of the sensor. In certain embodiments, information gathered by sensors is indicative a tissue condition (e.g., healthful, diseased, active, inactive, stimulated, and ablated) in a proximity of the sensor.

In certain embodiments, an electrode probe, an auxiliary probe, or both can comprise insulating elements effective to reduce or block energy delivery from an electrode to a non-target tissue in a proximity of a target motor neuron branch, and thereby focus energy delivery to a specific region of tissue. In certain embodiments, an electrode probe and/or an auxiliary probe comprising an insulating element can achieve asymmetric energy delivery. In certain embodiments, an electrode probe and/or an auxiliary probe comprising an insulating element can achieve symmetric energy delivery. Insulating elements can be made from a variety of materials, such as Teflon®, PTFE, a polyimide material, a polyamide material, or other insulative material. The insulating material may be coated, bonded, glued, welded, etc. onto an electrode or other component of an electrode probe or onto an auxiliary probe.

In certain embodiments, an electrode probe comprises a metal, such as stainless steel, nickel, titanium, platinum, aluminum, iron, and alloys thereof. In certain embodiments, an electrode probe comprises an electromagnetic energy transmission element. In certain embodiments, an electromagnetic energy transmission element can be configured to transmit electromagnetic radiation in wavelengths and amounts effective to illuminate, to stimulate, and/or to photoablate a tissue in a proximity of the electrode, and such transmitted electromagnetic radiation can comprise, e.g., at least one wavelength selected from ultraviolet, blue, red, visible, infrared, radio, and microwave.

In certain embodiments, an electrode probe comprises energy transmission elements configured to transmit heat energy, cryogenic energy, or a combination thereof. Such heat and cryogenic energy transmission elements can be configured to transmit heat or cryogenic, energy, respectively, in amounts effective to stimulate and/or ablate a tissue in a proximity of an electrode. In certain embodiments, an electrode probe comprises an ultrasonic energy transmission element, and ultrasonic energy transmission elements can be configured to transmit ultrasonic energy in amounts effective to stimulate and/or to ablate a tissue in a proximity of the electrode.

In certain embodiments, an electrode probe comprises at least one of an electromagnetic transmission element, a heat energy transmission element, cryogenic energy transmission element, and an ultrasonic energy transmission element. In certain embodiments, electrodes comprise at least one metal, such as stainless steel, nickel, titanium, platinum, aluminum, iron, and alloys thereof. In certain embodiments, electrodes comprising multiple metals and/or alloys can be joined by, e.g., crimping, swaging, soldering, welding, and/or adhesive bonding.

In certain embodiments, the electrode probe can include features from the device disclosed in U.S. patent application Ser. No. 10/870,202, filed on Jun. 17, 2004, and incorporated by reference herein in its entirety.

Control Units

In certain embodiments, an energy delivery device can comprise, or be coupled to, one or more control units. A control unit can configure an amount of energy and a temporal pattern of energy provided by an energy generating unit to one or a plurality of electrode probes and/or energy transmission members, either automatically (e.g., by running a microprocessor program), under the control of an operator, (e.g., by one or more manual input interfaces), or by a combination of automatic and manual inputs.

Stimulation Energy

In certain embodiments, an amount of energy provided by an energy generating unit can be controlled to be stimulatory toward, for instance, a nerve, a branch of a nerve, a muscle, or combinations thereof; and such stimulatory energy can be effective to result in a depolarization of a nerve, a muscle, or both. In certain embodiments, a stimulation energy delivered by an energy transmission member to a muscle, a nerve, or both, can be effective to result in a muscle contraction.

In certain embodiments, a stimulatory amount of electromagnetic energy can be provided by an energy generating unit in the form of laser energy in a range from about 0.1 mJ to about 5 mJ with a spot size of about 5 .mu.m to about 600 .mu.m. In certain embodiments, a stimulatory amount of electromagnetic energy can be provided in the form of laser energy of about 1 mJ, about 2 mJ, about 3 mJ, about 4 mJ, and about 5 mJ. In certain embodiments, a stimulatory amount of electromagnetic energy can be provided in a laser comprising a beam width of about 5 .mu.m, about 10 .mu.m, about 20 .mu.m, about 30 .mu.m, about 40 .mu.m, 50 .mu.m, about 100 .mu.m, about 200 .mu.m, about 300 .mu.m, about 400 .mu.m, about 500 .mu.m, and about 600 .mu.m. In certain embodiments, a stimulatory amount of laser energy can be delivered in micropulses having a duration of about 1 ps, about 2 ps, about 3 ps, about 4 ps, about 5 ps, about 6 ps, about 7 ps, about 8 ps, about 1 ps, about 10 ps, about 15 ps, about 20 ps, about 30 ps, about 50 ps, and about 100 ps. An envelope of such micropulses can form a macropulse of about 1 .mu.s, about 2 .mu.s, about 5 .mu.s, about 10 .mu.s, about 20 .mu.s, about 30 .mu.s, about 40 .mu.s, about 50 .mu.s, about 75 .mu.s, and about 100 .mu.s. In certain embodiments, a macropulse of stimulatory laser energy can be delivered at a rate of about 1 Hz, about 5 Hz, about 10 Hz, about 20 Hz, about 30 Hz, about 40 Hz, about 50 Hz, about 75 Hz, and about 100 Hz.

Electromagnetic energy absorption characteristics of many biological tissues, such as nerve tissue and muscle tissue, often closely corresponds to the electromagnetic energy absorption characteristics of water. In certain embodiments, photoablation of biological tissues can be minimized or avoided in the process of delivering a stimulatory amount of electromagnetic energy by providing electromagnetic energy in wavelengths poorly absorbed by water, such as wavelengths of about 1 .mu.m, about 1.25 .mu.m, about 1.5 .mu.m, about 1.75 .mu.m, about 2 .mu.m, about 2.25 .mu.m, about 2.5 .mu.m, about 2.75 .mu.m, about 2.75 .mu.m, about 4 .mu.m, about 4.25 .mu.m, about 4.5 .mu.m, about 4.75 .mu.m, about 5 .mu.m, about 5.25 .mu.m, and about 5.5 .mu.m.

In certain embodiments, a free electron laser (FEL), tunable in to provide infrared spectrum electromagnetic wavelengths from about 2 .mu.m to about 10 .mu.m, can provide stimulatory electromagnetic energy. In certain embodiments, a FEL can provide stimulatory electromagnetic energy in micropulses, each about 1 ps in duration, with a repetition rate of about 3 GHz. The envelope of such micropulses can form a macropulse of about 1 .mu.s to about 10 .mu.s, which can be delivered at a rate of up to about 30 Hz.

In certain embodiments, an energy generating unit can be configured to provide a stimulatory amount of electrical energy in the form of electrical energy, such as low frequency DC energy pulses of, e.g., about 0.1 Hz, about 0.5 Hz, about 1 Hz, about 2 Hz, about 3 Hz, about 4 Hz, about 5 Hz, about 6 Hz, about 7 Hz, about 8 Hz, about 9 Hz, and about 10 Hz, at low amps of, for instance, about 0.1 mA, about 0.25 mA, about 0.5 mA, about 0.75 mA, about 1 mA, about 2 mA, about 3 mA, about 4 mA, about 5 mA, about 10 mA, about 15 mA, about 20 mA, and about 25 mA, without generating an ohmic heating effect. Such neurostimulatory electrical energy can be applied as DC square pulses having a pulse width of about 1 ms, about 10 ms, about 25 ms, about 50 ms, about 75 ms, about 100 ms, about 125 ms, about 150 ms, about 175 ms, and about 200 ms.

In certain embodiments, an energy generating unit can provide a stimulatory amount of electrical energy in the form of electrical energy comprising an amplitude of about 1 mA, about 2 mA, about 3 mA, about 4 mA, about 5 mA, about 6 mA, about 7 mA, about 8 mA, about 9 mA, about 10 mA; a pulse width of about 0.1 ms, about 0.2 ms, about 0.3 ms, about 0.4 ms, about 0.5 ms, about 0.6 ms, about 0.7 ms, about 0.8 ms, about 0.9 ms, and about 1 ms; and a frequency of about 1 Hz, about 2 Hz, about 3 Hz, about 4 Hz, and about 5 Hz.

In certain embodiments, an activity of a biological tissue, e.g., muscle or nerve tissue, resulting from the delivery, to a second or higher-order postganglionic nerve branch or other nerve of a patient's head, can be observed visually as, e.g., a muscle twitch or electrically by an electrode configured to detect a depolarization of the nerve.

Ablation Energy

In certain embodiments, an amount of energy provided by an energy generating unit can be controlled to result in an ablation of a nerve, a branch of a nerve, or both. In certain embodiments, an ablative amount of electromagnetic energy can be provided in the form of laser energy in a range from about 2.5 mJ to about 250 mJ with a spot size of about 5 .mu.m to about 1000 .mu.m. In certain embodiments, an ablative amount of laser energy can be provided in the form of pulsed laser energy of about 1 mJ, about 3 mJ, about 5 mJ, about 10 mJ, about 20 mJ, about 30 mJ, about 40 mJ, about 50 mJ, about 75 mJ, about 100 mJ, about 150 ml, about 200 ml, and about 250 mJ and can comprise a spot size of about 5 .mu.m, about 10 .mu.m, about 20 .mu.m, about 30 .mu.m, about 40 .mu.m, 50 .mu.m, about 100 .mu.m, about 200 .mu.m, about 300 .mu.m, about 400 .mu.m, about 500 .mu.m, about 600 .mu.m, about 700 .mu.m, about 800 .mu.m, about 900 .mu.m, and about 1000 .mu.m.

In certain embodiments, an ablative amount of laser energy can be delivered in micropulses having a duration of about 10 ps, about 20 ps, about 50 ps, about 100 ps, about 250 ps, about 500 ps, about 1 ns, about 10 ns, about 25 ns about 50 ns, about 75 ns, and about 100 ns. An envelope of such micropulses can form a macropulse of about 1 .mu.s, about 10 .mu.s, about 25 .mu.s, about 50 .mu.s, about 100 .mu.s, about 250 .mu.s, about 500 .mu.s, about 750 .mu.s, about 1 ms, about 10 ms, about 50 ms, and about 100 ms. In certain embodiments, a macropulse of stimulatory electromagnetic energy can be delivered at a rate of about 1 Hz, about 5 Hz, about 10 Hz, about 20 Hz, about 30 Hz, about 40 Hz, about 50 Hz, about 75 Hz, and about 100 Hz.

In certain embodiments, the stimulatory amount of electromagnetic energy, the ablative amount of electromagnetic energy, or both, can be provided by, e.g., a YAG laser, tunable to provide electromagnetic wavelengths in the UV, visible, and infrared portion of the spectrum or a lead-salt laser, tunable to provide wavelength of about 4 .mu.m.

In certain embodiments, a control unit can be coupled to an energy generating unit, a laser transmission element, and a sensor that, together, facilitate automatic adjustment of laser delivery parameters, e.g., pulse duration, repetition rate, spot size, and total amount of laser energy based on a sensed condition of the tissue to which the laser energy is delivered so as to achieve a desired condition, e.g. temperature, of the target tissue. In some embodiments, automatic shutoff of the laser occurs upon reaching the desired condition the laser energy delivery. This enables control and optimization of the desired effect (e.g., stimulation and/or ablation) of laser energy delivery on the target tissues.

In certain embodiments, an ablative amount of electromagnetic energy can be provided in the form of radiofrequency (RF) energy of, for instance, about 100 kHz, about 250 kHz, about 500 kHz, about 750 kHz, about 1 mHz, about 2.5 mHz, about 5 mHz, about 7.5 mHz, and about 10 mHz applied at, for instance, about 0.1 A, about 0.25 A, about 0.5 A, about 1 A, about 2 A, about 5 A, and about 10 A.

In certain embodiments, the delivery of an ablative amount of RF energy, heat energy, laser energy, electric energy, or combinations thereof can result in a temperature of a target nerve of about 40.degree. C., about 45.degree. C., about 50.degree. C., about 55.degree. C., about 60.degree. C., about 70.degree. C., about 80.degree. C., about 90.degree. C., and about 100.degree. C. In certain embodiments, delivery of an ablative amount of cryogenic energy can result in a temperature of a target nerve, nerve branch, or both, of about −80.degree. C., about −70.degree. C., about −60.degree. C., about −50.degree. C., about −40.degree. C., about −30.degree. C., about −20.degree. C., about −10.degree. C., and about 0.degree. C.

In certain embodiments, a control unit can configure an RF transmission element of an electrode probe to operate as a RF energy transmitter or as a RF energy receiver. A control unit can provide for monopolar operation of an electrode probe by configuring multiple RF transmission elements of an electrode probe to transmit RF energy to a common RF energy receiver. In certain embodiments, a control unit can provide for bipolar operation of an electrode probe by configuring pairs of RF transmission elements of an electrode probe such that one electrode of the pair operates as a RF energy transmitter and the other operates as a RF energy receiver. In certain embodiments, a control unit can switch, randomly or in an ordered sequence, the transmitter and receiver operations of RF energy transmission elements within a pair as well the identity of electrode probes operative as a pair. In certain embodiments, electrodes probes configured to deliver RF energy can also be configured to deliver neurostimulatory electrical energy, as described herein.

In certain embodiments, the control of energy delivery afforded by a control unit allows temporary nerve-conduction interruption that is permanent or temporary, which can last for a period of several months or years. This flexibility allows for patients and physicians to evaluate temporary treatment before choosing longer or permanent treatment options.

Neurotoxins

In certain embodiments, neurotoxins capable of producing reversible muscle paralysis without a concomitant degeneration of muscle or nervous tissue can be administered, in a therapeutically effective amount that reduces a headache pain in a patient, to a neuron in combination with the delivery of neurostimulatory and neuroablative energy as described herein. In certain embodiments, a neurotoxin is a Botulinum toxin, such as Botulinum toxin A and tetanus toxin.

In certain embodiments, a neurotoxin can be administered to reduce a head pain associated with muscle spasm, muscle contraction, vascular disturbances, neuralgia, and neuropathy. In certain embodiments, a neurotoxin can be administered intramuscularly to reduce headache pain, and an amount of administered neurotoxin effective to reduce headache pain does not result in paralysis of a muscle. In certain embodiments, an amount of administered neurotoxin effective to reduce headache pain does result in a paralysis of a muscle.

As used herein, the term "Neurotoxin" includes invertebrate protein toxins and biologically active peptide fragments thereof. In certain embodiments, a neurotoxin comprises Botulinum toxin. Serotype A of this toxin is commercially available under the tradename BOTOX®. In certain embodiments, a neurotoxin comprises a pentavalent toxoid composition of all eight known Botulinum serotypes. In certain embodiments, a neurotoxin comprises a subcombination of the eight known Botulinum serotypes. In certain embodiments, a neurotoxin can comprise a tetanus toxin and/or a biologically active peptide fragments thereof, such as the Ibc fragment of tetanus toxin. In certain embodiments, a neurotoxin can comprise a form that is nontetragenic and does not induce a detectable immune response to the toxin antigen. In certain embodiments, a neurotoxin can be administered in a pharmaceutical composition comprising pharmaceutically acceptable salts, buffers, carriers, chelating agents, excipients, and combinations thereof.

A therapeutically effective dose of a neurotoxin to be administered can vary with the age, condition, and weight of the patient to be treated as well as the site and method of administration of the neurotoxin, the stimulatory energy, and the ablative energy. The potency of the neurotoxin will also be considered. In certain embodiments, a therapeutically effective dose of a neurotoxin can be about 1 pg, about 10 pg, about 25 pg, about 50 pg, about 100 pg, about 250 pg, about 500 pg, about 750 pg, about 1 ng, about 10 ng, about 25 ng, about 50 ng, and about 100 ng. In certain embodiments, a therapeutically effective dose of a neurotoxin can be about 1 microunit, about 5 microunits, about 10 microunits, about 20 microunits, about 50 microunits, about 100 microunits, about 250 microunits, about 500 microunits, about 750 microunits, about 1 milliunit, about 5 milliunits, about 10 milliunits, about 20 milliunits, about 50 milliunits, about 100 milliunits, about 250 milliunits, about 500 milliunits, about 750 milliunits, about 1 unit, about 5 units, about 10 units, about 20 units, and about 50 units. As used herein, one unit of a neurotoxin is an amount of toxin that kills 50% of a group of mice that were disease-free prior to inoculation with the toxin.

In certain embodiments, a neurotoxin can be administered by injection. In certain embodiments, a low dosage of a neurotoxin may initially be administered at a target region to determine the patient's sensitivity to, and tolerance of, the neurotoxin. Additional injections of the same or different dosages can be administered as necessary. In certain embodiments, a neurotoxin can be administered by subcutaneous injection, perivascular injection, or intramuscular injection (e.g., to a neuromuscular endplate or neuromuscular junction of a secondary or higher order postganglionic nerve branch, or other, ablated in a patient according to a method for treating headache disclosed herein).

In certain embodiments, the administration of a neurotoxin and neuroablative energy can occur simultaneously or sequentially in a single procedure or in multiple procedures. In certain embodiments, injections of a neurotoxin can be repeated as necessary. For instance, Botulinum toxin A administered into or near muscle tissue typically produces flaccid paralysis at target site muscles for up to about 3 to about 6 months. Reduction of headache pain in patients who received the neurotoxins extramuscularly can also persist for extended periods of time, such as up to about 3 to about 6 months.

In certain embodiments, intramuscular injection of a neurotoxin can involve an electromyographical ("EMG") injection, in which the neurotoxin is administered percutaneously into a target site, such as a muscle comprising a neuromuscular junction. For instance, a monopolar hollow bore needle can be inserted through skin, and its position adjusted, based on observation of the EMG signal, such that the neurotoxin is delivered to the neuromuscular junction without substantial systemic distribution.

EXAMPLES

Twenty patients, each of whom suffered from migraine headaches, were entered into a single arm efficacy study of selective percutaneous neurolysis treatment method. Prior to and after treatment, each patient answered questionnaires. Pretreatment questionnaires established that 13 of the 20 patients suffered migraine headaches more than 15 days per month and that 7 of the 20 patients suffered from migraine headaches less than 15 days per month. Pretreatment questionnaires established that 5 of the 20 patients suffered from migraine headaches lasting for more than 72 hours; 11 of the 20 patients suffered from migraine headaches lasting for 4 to 72 hours, and 4 of the 11 patients suffered from migraine headaches lasting for less than 4 hours. Pretreatment questionnaires established that 15 of the 20 patients suffered severe disability resulting from migraine headache and that 5 of the 20 patients suffered from mild or no disability resulting from migraine headache. Post treatment questionnaires established that, following a selective percutaneous neurolysis treatment, 10 of the 20 patients experienced a decrease in migraine headache frequency; 10 of the 20 patients experienced no decrease in migraine headache frequency; 1 of the 20 patients experienced an increase in migraine headache event frequency; 14 of the 20 patients experienced reduced disability resulting from migraine headache; 4 of the 20 patients experienced no change in disability resulting from migraine headache; 2 of the 20 patients experienced increased disability resulting from migraine headache. Overall, 18 of the 20 patients had a decrease in at least one migraine headache symptom.

The present disclosure is capable of embodiments additional to those described herein, and the disclosure is not limited in its application to the embodiments described herein, or to the details of the particular embodiments described herein. The terminology used herein is for the purpose of describing the headache treatment methods of the present disclosure, and the present disclosure, as described herein, has numerous equivalents within its scope.

I claim:

1. A treatment method comprising:
   providing an energy delivery device;
   locating a secondary or higher-order branch of a postganglionic nerve that provides innervation for a patient's head, wherein the locating comprises:
   identifying a target region, of the patient's head, comprising the nerve branch;
   percutaneously advancing a portion of the energy delivery device to position the portion of the energy delivery device within the target region; and
   applying, from the positioned portion of the energy delivery device to the target region, an amount of energy effective to result in a stimulation activity of the nerve branch; and
   after observing the stimulated nerve branch activity, delivering, from the energy delivery device to the nerve branch, energy in an amount effective to effect the treatment in the patient.

2. The method of claim 1, wherein the treatment comprises at least one of a reducing degree of pain, reducing a frequency of the pain, and a reducing a of the pain.

3. The method of claim 1, wherein the nerve branch comprises a motor neuron, a sympathetic neuron, or a tertiary or higher-order branch.

4. The method of claim 1, further comprising at least one of detecting the stimulated nerve branch activity with electromyography, and detecting the stimulated nerve branch activity as nerve conduction between two electrodes.

5. The method of claim 1, further comprising: locating a sensory nerve innervating the patient's head; and applying, from the positioned portion of the energy delivery device to the sensory nerve, an amount of energy effective to reduce the pain severity in the patient.

6. The method of claim 5, wherein the sensory nerve comprises at least one of a second occipital nerve, a third occipital nerve, a zygomaticotemporal nerve, a trigeminal nerve, a glossopharyngeal nerve.

7. The method of claim 1, wherein the delivered energy comprises at least one of ultrasound energy, heat energy, cryogenic energy, electromagnetic energy, ultraviolet light energy, a blue light energy, an infrared light energy, an x-ray energy, a gamma-ray energy, and a microwave energy.

8. The method of claim 1, wherein the amount of delivered energy effective to reduce the pain is effective to ablate the neuron.

9. The method of claim 3, wherein the motor neuron innervates a muscle selected from the group consisting of a frontalis muscle, a corrugator superculii muscle, an orbicularis oculi muscle, a procerus muscle, a nasalis muscle, a levator labii superioris muscle, a zygomaticus major muscle, a zygomaticus minor muscle, a levator anguii oris muscle, a modialus muscle, a platysma paris muscle, a platysma labialis muscle, a depressor labii inferioris muscle, a depressor anguli oris muscle, a platysma pars modialaris muscle, a platysma pars labialis muscle, a platysma pars mandibularis muscle, a temporalis muscle, an occipatal is muscle, a risorius muscle, a masseter muscle, a splenius capitus muscle, a stylohyoid muscle, a suboccipital muscle, a digastric muscle, a buccinator muscle, a sternocleidomastoid muscle, a levator scapulae muscle, a scalenus medius muscle, a scalenus anterior muscle, a trapezius muscle, and an omohyoid muscle.

10. The method of claim 3, wherein the nerve is selected from at least one of a facial nerve, an abducens nerve, an oculomotor nerve, a trochlear nerve, a trigeminal nerve, a glossopharangeal nerve, a hypoglossal nerve, and an accessory nerve.

11. The method of claim 3, wherein the nerve branch comprises a branch of a facial nerve selected from a temporal branch, a zygomatic branch, a buccal branch, a mandibular branch, and a cervical branch.

12. The method of claim 3, wherein the nerve branch is selected from at least one of a superior division of the oculomotor nerve and art inferior division of the oculomotor nerve.

13. The method of claim 3, wherein the nerve branch comprises a mandibular branch of the trigeminal nerve, a mylohyoid branch of the mandibular branch, or a pharyngeal branch of the glossopharyngeal nerve.

14. The method of claim 3, wherein the nerve branch comprises a branch of the hypoglossal nerve selected from a meningeal branch, a thyrohyoid branch, a descending branch, and a muscular branch.

15. The method of claim 3, wherein the nerve branch comprises an angular nerve.

16. A method, of treating head pain, comprising:
providing an energy delivery device having a single tip;
locating a secondary or higher-order branch of a post-ganglionic nerve that provides innervation for a patient's head, wherein the locating comprises:
identifying a target region, of the patient's head, comprising the nerve branch; percutaneously advancing a portion of the energy delivery device through a single point to position the portion of the energy delivery device within the target region; and
applying, from the positioned portion of the energy delivery device to the target region, an amount of energy effective to result in a stimulation activity of the nerve branch;
after observing the stimulated nerve branch activity:
delivering, from the energy delivery device to the nerve branch, energy in an amount effective to reduce a pain severity in the patient; and administering, to a target area of the patients head comprising a motor neuron, a neurotoxin;
wherein, in combination, the amount of delivered energy and the amount of administered neurotoxin are effective to reduce the pain severity in the patient.

17. The method of claim 16, wherein the delivered energy comprises at least one of ultrasound energy, heat energy, cryogenic energy, electromagnetic energy, ultraviolet light energy, a blue light energy, an infrared light energy, an x-ray energy, a gamma-ray energy, and a microwave energy.

18. The method of claim 16, wherein the nerve branch comprises a motor neuron, a sympathetic neuron, or a tertiary or higher-order branch.

19. The method of claim 18, wherein the motor neuron innervates a muscle selected from the group consisting of a frontalis muscle, a corrugator superculii muscle, an orbicularis oculi muscle, a procerus muscle, a nasalis muscle, a levator labii superioris muscle, a zygomaticus major muscle, a zygomaticus minor muscle, a levator anguii oris muscle, a modialus muscle, a platysma paris muscle, a platysma labialis muscle, a depressor labii inferioris muscle, a depressor anguli oris muscle, a platysma pars modialaris muscle, a platysma pars labialis muscle, a platysma pars mandibularis muscle, a temporalis muscle, an occipatalis muscle, a risorius muscle, a masseter muscle, a splenius capitus muscle, a stylohyoid muscle, a suboccipital muscle, a digastric muscle, a buccinator muscle, a sternocleidomastoid muscle, a levator scapulae muscle, a scalenus medius muscle, a scalenus anterior muscle, a trapezius muscle, and an omohyoid muscle.

20. The method of claim 18, wherein the nerve branch comprises a mandibular branch of the trigeminal nerve, a mylohyoid branch of the mandibular branch, or a pharyngeal branch of the glossopharyngeal nerve.

* * * * *